United States Patent [19]
Cross

[11] Patent Number: 5,605,161
[45] Date of Patent: Feb. 25, 1997

[54] DISPOSABLE URINALYSIS DEVICE WITH INDICATOR

[76] Inventor: Leta K. Cross, 169 Sage Rd., Houston, Tex. 77056-1417

[21] Appl. No.: 265,228

[22] Filed: Jun. 24, 1994

[51] Int. Cl.$^6$ .................................................. A61B 5/00
[52] U.S. Cl. ........................ 128/771; 128/761; 128/767; 4/144.2
[58] Field of Search ..................... 128/761, 767, 128/771; 604/329, 347, 349; 4/144.2, 144.3

[56] References Cited

U.S. PATENT DOCUMENTS

| | | | |
|---|---|---|---|
| 1,407,872 | 2/1922 | Lacy. | |
| 2,066,400 | 1/1937 | Hale. | |
| 2,182,254 | 12/1939 | Farrell. | |
| 2,690,568 | 10/1954 | Willis. | |
| 3,329,973 | 7/1967 | Bobbe. | |
| 3,597,770 | 8/1971 | Jacuzzi et al.. | |
| 3,613,122 | 10/1971 | Gross et al.. | |
| 3,774,455 | 11/1973 | Seidler et al. | 128/771 |
| 4,023,216 | 5/1977 | Li. | |
| 4,305,161 | 12/1981 | Diaz | 4/144.2 |
| 4,528,703 | 7/1985 | Kraus | 4/144.2 |
| 4,531,245 | 7/1985 | Lowd et al. | 4/144.3 |
| 4,608,046 | 8/1986 | Towfigh | 604/329 |
| 4,681,573 | 7/1987 | McGovern et al. | 604/329 |
| 4,751,751 | 6/1988 | Reno | 4/144.3 |
| 4,815,151 | 3/1989 | Ball | 4/144.3 |
| 4,911,698 | 3/1990 | Wapner | 604/329 |
| 4,937,889 | 7/1990 | Strickland | 4/144.3 |
| 4,937,890 | 7/1990 | Tafur | 4/144.4 |
| 5,004,463 | 4/1991 | Nigay | 604/329 |
| 5,007,116 | 4/1991 | Yamamoto | 4/144.2 |
| 5,010,559 | 4/1991 | Nilsson | 4/144.2 |
| 5,065,459 | 11/1991 | Tjahaja et al. | 4/144.2 |
| 5,091,998 | 3/1992 | Irazabal | 4/144.4 |
| 5,125,118 | 6/1992 | Green | 4/144.2 |
| 5,235,705 | 8/1993 | Belisle | 4/144.3 |
| 5,243,712 | 9/1993 | Cross | 4/144.2 |
| 5,312,379 | 5/1994 | Rahe | 128/771 |
| 5,368,583 | 11/1994 | Fleury | 128/771 |
| 5,423,792 | 6/1995 | Oxley | 128/771 |

FOREIGN PATENT DOCUMENTS 2565956  6/1984  France.

Primary Examiner—Max Hindenburg

[57] ABSTRACT

A disposable urinary device (10, 50) comprises a collapsible funnel-shaped body (12) extending between an upper substantially rigid rim (16) and a lower discharge opening (14). The body (12) is provided with a pair of positioning loops (30) for positioning the urinary device (10, 50) against the body of the user for directing urine away from the body of the user while urinating in an upright position. Chemical reagent test strips (38, 56, and 94) secured to the interior of the body (12) are detached from the body (12) after exposure to urine for urinalysis.

15 Claims, 2 Drawing Sheets

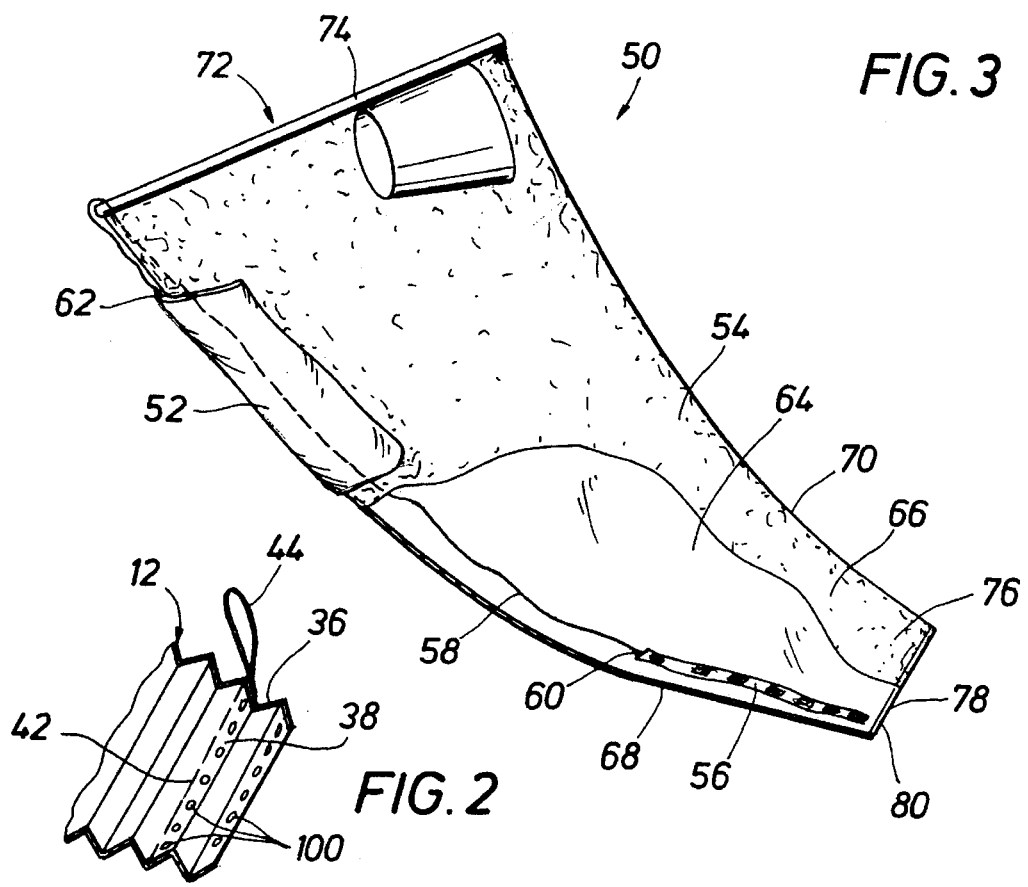
FIG. 3
FIG. 2
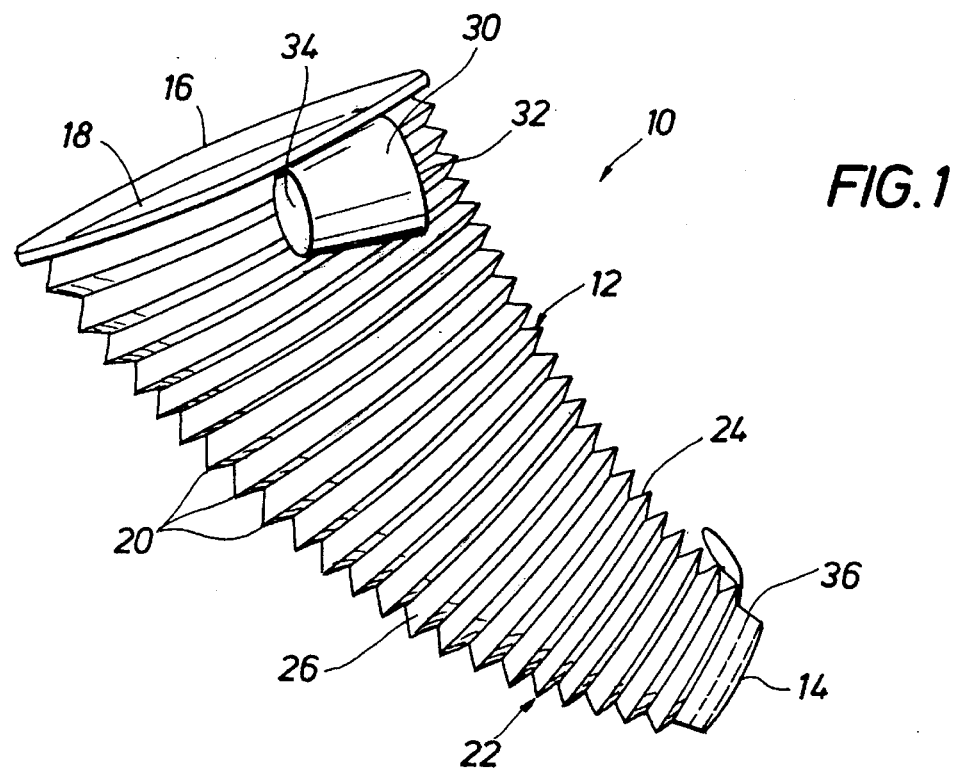
FIG. 1

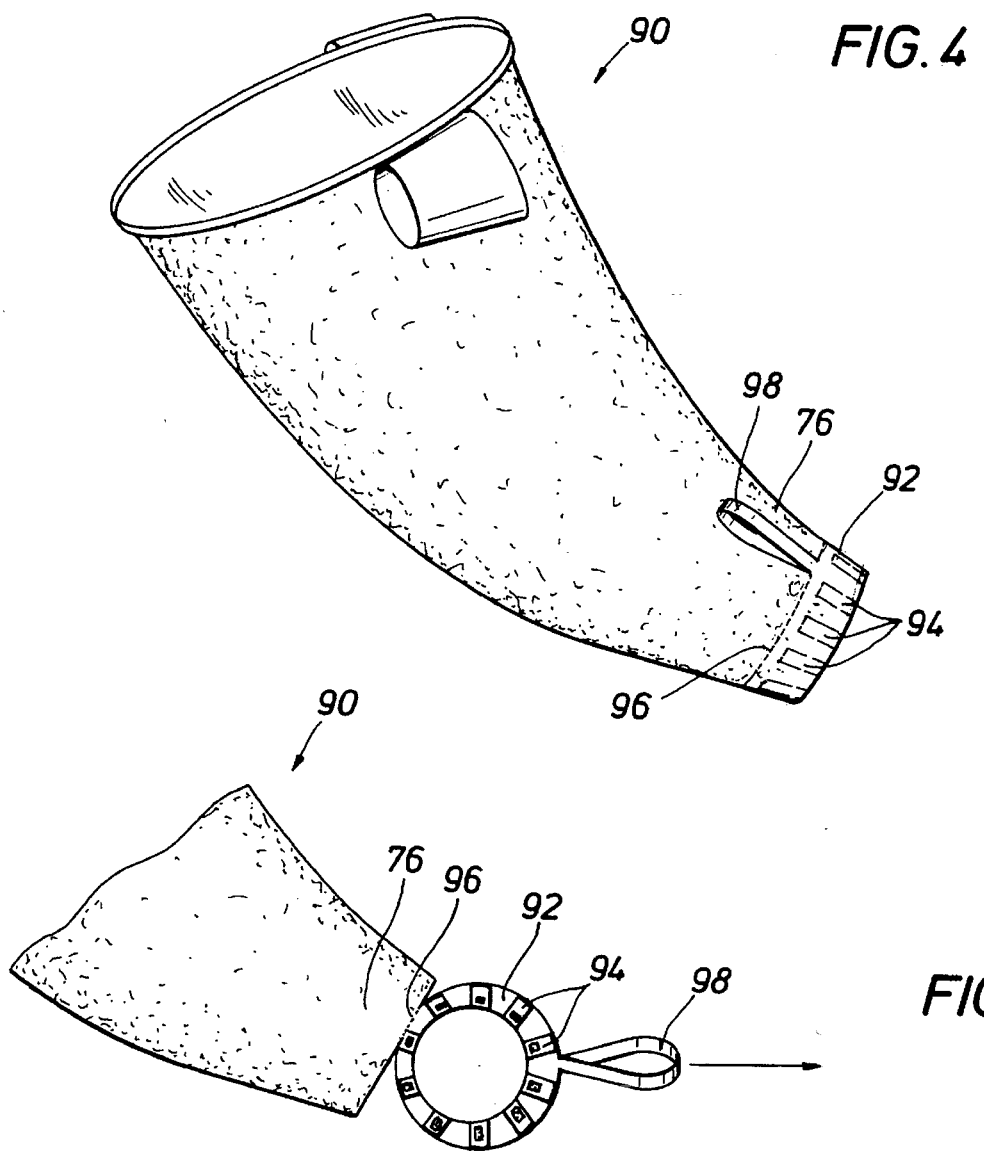
FIG. 4
FIG. 5
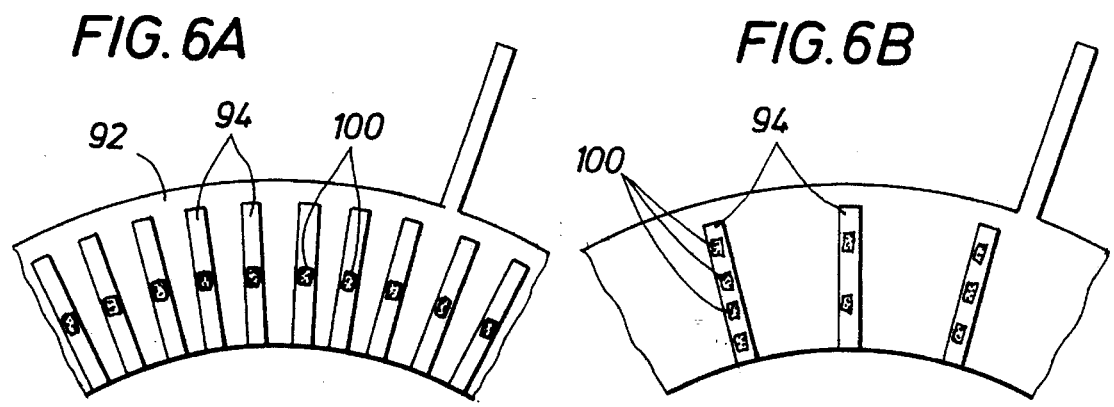
FIG. 6A
FIG. 6B

DISPOSABLE URINALYSIS DEVICE WITH INDICATOR

This application is a continuation-in-part application of international application serial number PCT/US93/08595 filed Sep. 13, 1993.

BACKGROUND OF THE DISCLOSURE

This invention relates to urinalysis devices. More particularly, the invention relates to a disposable urinary device for use by males or females to facilitate urinalysis without getting urine on the hands or clothes.

Urine samples are known to have certain constituents which are useful indicators of the health or condition of the individual from which it was taken. For example, urine may be tested for glucose, bilirubin, pH, protein, leukocytes, and the like. For these reasons, urine samples are a common part of routine physicals as well as certain diagnostic testing. Typically, individuals must urinate into a small plastic bottle and take it to a laboratory for analysis.

Urinating into a small bottle can often be difficult to accomplish without soiling one's body or clothing, particularly for a female. Urine specimens are normally collected in small bottles or containers which are usually not adapted for convenient use in directing urine into the specimen container. For most females, for example, it is awkward and difficult to gather a urine specimen in such a container without splashing urine on the body or clothing.

Urinary devices to aid females to urinate from an upright position have been disclosed in the prior art. Various devices, such as those disclosed in U.S. Pat. No. 3,329,973 (Bobbe), U.S. Pat. No. 4,608,046 (Towfigh), U.S. Pat. No. 4,681,573 (McGovern, et al.) and U.S. Pat. No. 4,751,751 (Reno) are representative of prior art attempts to provide a solution to a problem which is often encountered by females.

The cup-like device disclosed in U.S. Pat. No. 3,329,973 is open at the top end and closed at the bottom end. In use, the device is pressed directly against the body and positioned carefully to cover the opening of the urinary tract, the capacity of the device being adequate for a single use. In U.S. Pat. No. 4,608,046 the urinary aid includes an end which is insertable between the labia. Hand squeezing opens the insertable end of the urinary aid to form a urine receptive configuration which spread the labia as the device is pressed against the urinary meatus.

In U.S. Pat. No. 4,681,573 the urinary device comprises a flat blank which may be folded to form a conical-like urinary device. The device must be properly positioned and carefully held to cover the opening of the urinary tract during use. In U.S. Pat. No. 4,751,751 the funnel like urinary device includes an upper end which is curved to envelop the exterior of the female vaginal area and a lower end portion formed into a spout-like shape.

Thus, while attempts have been made in the past to provide urine collecting or directing devices, particularly for female use, these devices have been difficult to use and made no provision for urinalysis. These devices are bulky and in some instances require the user to assemble the funnel-like device which could leak. Some of these devices have been designed for reuse and must be cleaned after each use before storing in a handbag or the like for subsequent use. Such devices are awkward, unsanitary and inconvenient to use, particularly after initial use whereupon cleaning the device is required.

It is therefore a primary object of the present invention to provide a disposable urinalysis device for use by males or females to urinate from an upright position which is simple and easy to use while preventing soiling of the body or clothing. The urinalysis device of the present invention requires no assembly and is easily properly positioned and secured for use. Urinalysis tests strips are detachable positioned within the device and may be removed after exposure to urine and the urinary device discarded.

SUMMARY OF THE INVENTION

The present invention, in the preferred embodiment, is directed to a disposable urinary device for use by a female to facilitate urinalysis without splashing urine on her body or clothes. The urinary device is in the form of a cone or funnel. The funnel portion of the device may be folded or collapsed onto itself to present a substantially flat, compact profile. The invention contemplates one hand operation accomplished by inserting two fingers into a pair of loops positioned adjacent to the upper opening of the device. The upper opening of the urinary device is dimensioned to envelop the exterior of the female vaginal area when pressed against the body of the user. The urinary device includes urinalysis test strips, which, after exposure to the urine, are detached from the urinary device for urinalysis.

BRIEF DESCRIPTION OF THE DRAWINGS

So that the manner of achieving the above recited features and advantages of the present invention can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is side view of the urinary device of the invention depicting a collapsible pleated body;

FIG. 2 is a partial sectional view of the discharge end of the urinary device showing the reagent test strips secured within the urinary device of FIG. 1;

FIG. 3 is a side view of an alternative embodiment of the urinary device of the invention shown with a side detachable pouch for storage of the reagent test strip after it has been exposed to urine;

FIG. 4 is a perspective view of the urinary device of FIG. 3 showing a reagent test strip ring detachably connected to the discharge end of the urinary body;

FIG. 5 is a partial side view of the urinary device showing detachment of the reagent test strip ring shown in FIG. 4;

FIG. 6A is a partial plan view of the reagent test strips of FIGS. 4 and 5 depicting one reagent per strip; and FIG. 6B is a partial plan view of the reagent test strips of FIGS. 4 and 5 depicting multiple reagents per strip.

DETAILED DESCRIPTION OF THE PREFERRED EMBODIMENT

Referring first to FIG. 1, the urinary device of the present disclosure is generally identified by the referenced numeral 10. In the description of the preferred embodiment hereinafter set forth, the discussion is primarily focused on female use of the urinary device 10. It is understood, however, that the utility of the urinary device 10 is not limited solely to female use, but rather is equally applicable for male use.

The urinary device 10 is formed of a paper-like material which is completely disposable. The material of the device 10 is biodegradable and flushable. The outer surface of the body of the device 10 is absorbent and may be used as a wipe. Upon contact with water for a short period of time, the device 10 becomes pliant and easily flushes down a toilet without clogging the plumbing or otherwise hampering the disposal of waste through the toilet facilities.

The urinary device 10 of the present disclosure comprises a funnel-like one piece unitary body 12 open at each end and defining an axial passage extending between the open ends. The body 12 tapers downwardly and terminates at an outlet end 14. The upper end of the body 12 is open and defined by an upper edge 16. The upper edge 16 circumscribes an opening 18 conforming approximately to the contour of the female body which the opening 18 will circumscribe when the device 10 is in use.

The body 12 is horizontally pleated, thereby presenting an accordion-like profile. The plurality of pleats 20 permit the body 12 to be collapsed onto itself to form a substantially flat, compact profile. The flat profile is particularly desirable for individually packaging the urinary device 10 so that one or more may be conveniently carried in a typical handbag or the like. The flat profile of the urinary device 10 also lends itself to use with coin operated dispenser machines which may be located in public toilet facilities where the need for the urinary device 10 is the greatest. The urinary device 10 may thus be easily dispensed from a machine, used and discarded.

The pleated body 12 of the urinary device 10 tapers downwardly toward the discharge or outlet end 14. The pleats 20 decrease in diameter along the longitudinal length of the body 12 toward the outlet end 14. This permits the pleats 20 to collapse inwardly toward the longitudinal axis of the body 12, thereby forming a substantially flat profile having a maximum diameter defined by the upper edge or rim 16.

The lower portion of the body 12 forms a spout 22 terminating at the outlet end 14. The spout 22 extends angularly outwardly toward the front of the body 12, i.e., toward the right in FIG. 1, for directing urine forwardly away from the body of a female using the urinary device 10. The pleats 20 defining the spout 22 are gathered closer together along the front 24 of the body 12 than the back portion 26 of the body 12 so that the spout 22, when fully extended, is angularly directed relative to the longitudinal axis of the body 12. The spout 22 is relatively short for use by a female to urinate while standing. It is understood, however, that the spout 22 may be formed so that when it is extended it is sufficiently long for use by a female confined to a wheelchair or the like.

A pair of placement or positioning loops 30 are located on opposite sides of the rim 16 for holding the device 10 in proper position against the body when urinating. The loops 30 are adapted to receive the index and middle finger of a user and are positioned off center toward the front 24 of the device 10. The fingers of a user are inserted into the loops 30 and are spread to form a "V". With fingers spread, the user presses the rim 16 against the body thereby holding the urinary device 10 in a proper position for urination. The loops 30 are glued or otherwise attached adjacent the rim 16. The positioning loops 30 are substantially cylindrical in shape and open at both ends. The forward opening 32 is larger than the rear opening 34. Thus, the lower longitudinal sides of the positioning loops 30 are stitched at a slight angle downwardly toward the front 24 of the body 12. The larger positioning loop opening 32 permits the fingers of the user to be inserted through the positioning loops 30 so that the forward portion of the rim 16 fits against the fingers of the user which are spread to form a "V." The slight downward, angular orientation of the positioning loops 30 aides the user to properly position the urinary device 10 so that it angularly projects away from the body of the user.

In the preferred embodiment of the invention, the upper edge or rim 16 is outwardly rolled to form the substantially rigid rim 16. The rim 16, however, may be formed in any suitable fashion provided that sufficient rigidity is maintained for forming and maintaining the opening 18. While the rim 16 is sufficiently rigid to maintain the opening 18, the rim 16 is also sufficiently pliant so that it may be squeezed together or spread to accommodate variations in dimensions of the female anatomy.

In the embodiment of FIG. 1, the urinary device 10 includes a removable urinalysis reagent ring 36 coupled to the outlet end 14 of the body 12. The urinalysis ring 36 includes one or more reagent test strips having chemical reagent deposits on the inner surface thereof. In the embodiment of FIG. 2, the reagent test strips 38 are attached to the interior surface of one or more of the pleats 20 at the outlet end 14 of the body 12.

Referring again to FIG. 1, the urinalysis ring 36 is separable from the body 12 of the urinary device 10. While the urinalysis reagent ring 36 may be detached from the body 12 employing any number of detachment means, in the preferred embodiment perforations 42 are employed to define a weakened line around the ring 36. The outer surface of the ring 36 is provided with a tab or loop 44 which, when pulled, causes the perforations 42 to tear. In this manner, the ring 36 is quickly and easily removed and the loop 44 provides a clean, dry means for handling the ring 36.

In the preferred embodiment of FIG. 1, the urinary device 10 of the invention is collapsible, disposable and biodegradable. It is understood however that the urinary device 10 may also be formed of other materials which are non-collapsible and non-disposable. In addition, the body 12 of the urinary device 10 may be a straight funnel. Preferably, the urinary device 10 is formed of a paper-like material which is flushable and biodegradable. The interior surface of the body 12 is coated or lined with a water proof or water resistant material. The exterior surface of the body 12 is water absorbent and may be used as a self-wipe if desired. The external surface of the body 12 may also be impregnated with a deodorant or other hygienic composition.

Referring now to FIG. 3, an alternate embodiment of the urinary device of the invention, identified by reference numeral 50, is shown. The urinary device 50 comprises a funnel-like body 54. The body 54 of the urinary device 50 is defined at its upper end by the opening 72 which is circumscribed by the upper edge or rim 74. The lower end 76 of the body 54 is defined by the outlet opening 78.

A pouch 52 is attached to the body 54 for storage of a reagent test strip 56. The test strip 56 may be removed from the pouch 52 and placed inside the funnel-shaped body 54 for exposure to urine. The strip 56 is held in place by a string 58 connected to the strip at one end 60 and the pouch 52 or body 12 at a second end 62. The test strip 56 is positioned along the lower interior portion of the funnel-shaped body 54 and is easily removed after exposure to urine by pulling on the string 56. The pouch 52 and the point of attachment for the second end 62 of the string 58 are preferably located on the rearward portion of the body 54 of the urinary device 10.

Now referring to FIG. 4, the urinary device 90 is substantially similar to the urinary device 50 shown in FIG. 3, and therefore, like reference numerals have been used to indicate like components. The distal end 76 of urinary device 90 includes a removable band 92 having a plurality of reagent test strips 94 interiorly mounted thereon. The reagent strip band 92 is easily detached along perforations 96 by pulling on loop 98.

Referring now to FIG. 5, the urinalysis band 92 of FIG. 4 is shown being separated from the end 76 of the urinary device 90. The band is separated by pulling loop 98 away from the end 76. Perforations 96, or other means for defining where the separation will occur, enable the user to easily and quickly remove the reagent strip band 92 so that from the device 90 the exposed urinalysis reagents may be sent to a laboratory or other facility for analysis.

Now referring to FIG. 6A, the test strips 94 are shown in greater detail. The test strips 94 are arranged roughly parallel around the perimeter of the urinalysis band 92. Each test strip 94 has a single reagent 100 deposited thereon for exposure to the urine. The reagents 100 may each be different or duplicates of one or more reagent.

Conversely, FIG. 6B shows test strips 94 with multiple reagents 100 on each strip. This arrangement facilitates sending one or more reagent test strips 94 to a given laboratory or clustering a large number of reagent deposits 100 along the bottom surface of the opening.

The urinary device 10 is prepared for use by pulling the outlet end 14 outwardly from the rim 16 to form the funnel-shaped body 12 or alternatively, unfolding the body 12. For female use, the index and middle finger of the user are inserted in the loops 30 and the rim 16 is pressed directly against the female body for urination while standing. In this manner, urine is directed away from the user's body. Thus, the user avoids coming into physical contact with the toilet facilities. After use, the urinalysis reagent ring 36 is separated from the body 12 and stored in the pouch 52 or other suitable containers. Thereafter, the urinary device 10 may be used as a vaginal wipe and then discarded into the toilet bowl and flushed away.

While the foregoing is directed to the preferred embodiment of the present invention, other and further embodiments of the invention may be devised without departing from the basic scope thereof, and the scope thereof is determined by the claims which follow.

I claim:

1. A urinalysis device, comprising:
   a) a downwardly tapering, funnel-shaped unitary body defining an axial passage extending therethrough;
   b) a substantially rigid rim defining an upper end of the body, the rim circumscribing an opening forming the upper end of the body;
   c) a discharge opening defining a lower end of the body, the discharge opening being in fluid communication with the opening, wherein the discharge opening and the opening define opposite ends of the axial passage extending therebetween;
   d) positioning means secured adjacent to the rim for holding said body in position for use; and
   e) urinalysis means secured to said body by an adhesive strip for contacting with urine.

2. The urinalysis device of claim 1 wherein the urinalysis means comprises a reagent test strip.

3. The urinalysis device of claim 1 wherein the positioning means comprises a pair of loops secured opposite each other on said body adjacent the rim for holding said body in position generally circumscribing the female vaginal area.

4. The urinalysis device of claim 1 wherein said body includes a plurality of substantially horizontal pleats defining said body between the rim and the discharge opening.

5. The urinalysis device of claim 1 wherein the body is internally coated with a water resistant composition and the external surface of the body is sufficiently pliant for use as a self-wipe.

6. The urinalysis device of claim 5 wherein the external surface of the body is impregnated with a hygienic composition.

7. The urinalysis device of claim 1 wherein the funnel-shaped body is inwardly collapsible along its longitudinal axis for forming a substantially flat storage profile.

8. The urinalysis device of claim 1 wherein the urinalysis means comprises a reagent test strip ring detachably connected to said body.

9. The urinalysis device of claim 1 further including means for separating the urinalysis means from the body.

10. The urinalysis device of claim 9 wherein the means for separating comprises a line of perforations between the body and the urinalysis means and a pull tab attached to the urinalysis means.

11. The urinalysis device of claim 1 wherein the urinalysis means is attached to the body by a string.

12. A urinalysis device for female use, comprising:
   a) a downwardly tapering, funnel-shaped unitary body defining an axial passage extending therethrough;
   b) a substantially rigid rim defining an upper end of the body, the rim circumscribing an opening forming the upper end of the body;
   c) a discharge opening defining a lower end of the body;
   d) positioning means secured adjacent to the rim for positioning the funnel-shaped body to generally circumscribe the female vaginal area; and
   e) urinalysis means formed in the lower end of the body for contacting with urine, wherein the urinalysis means is detachably connected to the body along a line of perforations defining a tear line between the urinalysis means and the body.

13. The urinalysis device of claim 12 further including a tab coupled to the urinalysis means for detaching the urinalysis means along the tear line.

14. The urinalysis device of claim 12 wherein the body terminates in an angularly extending spout relative to the longitudinal axis of the funnel-shaped body upon extending the funnel-shaped body for use.

15. The urinalysis device of claim 12 wherein the urinalysis means comprises a reagent test strip.

* * * * *